(12) United States Patent
Ozinga et al.

(10) Patent No.: US 10,806,631 B2
(45) Date of Patent: Oct. 20, 2020

(54) SURGICAL TOOL FOR FORMING INCISIONS IN OCULAR TISSUE WITH TIP PROVIDING VISIBILITY AND RELATED APPARATUS AND METHOD

(71) Applicant: Refocus Group, Inc., Dallas, TX (US)

(72) Inventors: David G. Ozinga, Flower Mound, TX (US); David J. Schanzlin, San Diego, CA (US)

(73) Assignee: Refocus Group, Inc., Dallas, TX (US)

( * ) Notice: Subject to any disclaimer, the term of this patent is extended or adjusted under 35 U.S.C. 154(b) by 172 days.

(21) Appl. No.: 16/101,857

(22) Filed: Aug. 13, 2018

(65) Prior Publication Data

US 2019/0060124 A1 Feb. 28, 2019

Related U.S. Application Data

(60) Provisional application No. 62/549,318, filed on Aug. 23, 2017.

(51) Int. Cl.
*A61F 9/013* (2006.01)
*A61B 17/3211* (2006.01)

(52) U.S. Cl.
CPC ........ *A61F 9/0133* (2013.01); *A61B 17/3211* (2013.01); *A61B 2017/32113* (2013.01)

(58) Field of Classification Search
CPC ............................ A61F 9/0133; A61B 17/3211
See application file for complete search history.

(56) References Cited

U.S. PATENT DOCUMENTS

| 1,905,851 A | 4/1933 | Green |
| 2,104,929 A | 1/1938 | Kendall |
| 2,249,906 A | 7/1941 | Longoria |
| 2,580,138 A | 12/1951 | Trought |

(Continued)

FOREIGN PATENT DOCUMENTS

| CN | 1714761 A | 1/2006 |
| CN | 101854891 A | 10/2010 |

(Continued)

OTHER PUBLICATIONS

Michael R. Bryant et al., "Computer-Aided Surgical Design in Refractive Keratotomy", The CLAO Journal, vol. 13, No. 4, Jul. 1987, pp. 238-242.

(Continued)

*Primary Examiner* — Richard G Louis

(57) ABSTRACT

A surgical tool includes a housing having a driver and a surgical blade configured to be bi-directionally rotated by the driver. The surgical tool also includes a footplate configured to receive the surgical blade. The footplate includes a bottom portion configured to rest on ocular tissue of a patient's eye. The bottom portion includes a slot configured to allow passage of a portion of the surgical blade through the bottom portion of the footplate and into the ocular tissue of the patient's eye. The footplate also includes multiple walls having multiple openings. The openings are configured to receive additional portions of the surgical blade such that the surgical blade is rotatable relative to the footplate. The footplate further includes an additional opening or open side configured to allow viewing of the surgical blade and the slot during use.

20 Claims, 9 Drawing Sheets

(56) References Cited

U.S. PATENT DOCUMENTS

| | | | |
|---|---|---|---|
| 2,942,483 A | 6/1960 | Evans | |
| 3,609,864 A | 10/1971 | Bassett | |
| 3,814,213 A | 6/1974 | Balass | |
| 3,922,784 A | 12/1975 | Prince et al. | |
| 4,052,988 A | 10/1977 | Doddi et al. | |
| 4,071,029 A | 1/1978 | Richmond et al. | |
| 4,340,059 A | 7/1982 | Marinoff | |
| 4,349,027 A | 9/1982 | DiFrancesco | |
| 4,452,235 A | 6/1984 | Reynolds | |
| 4,601,290 A | 7/1986 | Effron et al. | |
| 4,649,919 A | 3/1987 | Thimsen et al. | |
| 4,669,466 A | 6/1987 | L'Esperance | |
| 4,672,964 A | 6/1987 | Dee et al. | |
| 4,688,570 A | 8/1987 | Kramer et al. | |
| 4,753,655 A | 6/1988 | Hecht | |
| 4,819,631 A | 4/1989 | Poley | |
| 4,955,882 A | 9/1990 | Hakky | |
| 4,986,807 A | 1/1991 | Farr | |
| 5,002,564 A | 3/1991 | McGregor et al. | |
| 5,006,123 A | 4/1991 | Soll et al. | |
| 5,090,955 A | 2/1992 | Simon | |
| 5,098,438 A | 3/1992 | Siepser | |
| 5,098,443 A | 3/1992 | Parel et al. | |
| 5,188,125 A | 2/1993 | Kilmer et al. | |
| 5,201,704 A | 4/1993 | Ray | |
| 5,203,865 A | 4/1993 | Siepser | |
| 5,215,104 A | 6/1993 | Steinert | |
| 5,222,959 A | 6/1993 | Anis | |
| 5,224,950 A | 7/1993 | Prywes | |
| 5,314,441 A | 5/1994 | Cusack et al. | |
| 5,342,377 A | 8/1994 | Lazerson | |
| 5,423,841 A | 6/1995 | Kornefeld | |
| 5,431,671 A | 7/1995 | Nallakrishnan | |
| 5,441,510 A | 8/1995 | Simpson et al. | |
| 5,492,528 A | 2/1996 | Anis | |
| 5,522,829 A | 6/1996 | Michalos | |
| 5,545,172 A * | 8/1996 | Knepshield | A61F 9/0133 30/293 |
| 5,547,468 A | 8/1996 | Simon et al. | |
| 5,571,106 A | 11/1996 | Coufal et al. | |
| 5,618,294 A | 4/1997 | Aust et al. | |
| 5,624,456 A | 4/1997 | Hellenkamp | |
| 5,651,782 A | 7/1997 | Simon et al. | |
| 5,695,511 A | 12/1997 | Cano et al. | |
| 5,700,274 A | 12/1997 | Feaster | |
| 5,779,723 A | 7/1998 | Schwind | |
| 5,817,115 A | 10/1998 | Nigam | |
| 5,908,433 A | 6/1999 | Eager et al. | |
| 6,007,578 A | 12/1999 | Schachar | |
| 6,033,437 A | 3/2000 | Perry | |
| 6,050,999 A | 4/2000 | Paraschac et al. | |
| 6,051,009 A | 4/2000 | Hellenkamp et al. | |
| 6,051,023 A | 4/2000 | Kilmer et al. | |
| 6,077,287 A | 6/2000 | Taylor et al. | |
| 6,080,172 A | 6/2000 | Fujiwara et al. | |
| 6,117,149 A | 9/2000 | Sorensen et al. | |
| 6,165,190 A | 12/2000 | Nguyen | |
| 6,171,336 B1 | 1/2001 | Sawusch | |
| 6,231,583 B1 | 5/2001 | Lee | |
| 6,264,668 B1 | 7/2001 | Prywes | |
| 6,328,747 B1 | 12/2001 | Nun | |
| 6,358,262 B1 | 3/2002 | Chan et al. | |
| 6,409,740 B1 | 6/2002 | Kuhr et al. | |
| 6,443,966 B1 | 9/2002 | Shiu | |
| 6,565,584 B1 | 5/2003 | Mathis et al. | |
| 6,602,266 B1 | 8/2003 | Loomas et al. | |
| 6,605,093 B1 | 8/2003 | Blake | |
| 6,610,075 B1 | 8/2003 | Levesque et al. | |
| 6,692,524 B2 | 2/2004 | Baikoff | |
| 6,926,727 B2 | 8/2005 | Schachar et al. | |
| 7,189,248 B2 | 3/2007 | Schachar et al. | |
| 7,763,042 B2 | 7/2010 | Iio et al. | |
| 7,901,421 B2 | 3/2011 | Shiuey et al. | |
| 8,201,942 B2 | 6/2012 | Williamson et al. | |
| 2002/0077642 A1 | 6/2002 | Patel et al. | |
| 2002/0116062 A1 | 8/2002 | Portney | |
| 2002/0120284 A1 | 8/2002 | Schachar et al. | |
| 2002/0120285 A1 | 8/2002 | Schachar et al. | |
| 2003/0097080 A1 | 5/2003 | Esashi et al. | |
| 2003/0120295 A1 | 6/2003 | Simpson et al. | |
| 2004/0073303 A1 | 4/2004 | Schanzlin et al. | |
| 2004/0220600 A1 | 11/2004 | Waldock et al. | |
| 2004/0243159 A1 | 12/2004 | Shiuey | |
| 2005/0131441 A1 | 6/2005 | Iio et al. | |
| 2006/0106408 A1 | 5/2006 | Schachar et al. | |
| 2006/0106409 A1 | 5/2006 | Schachar et al. | |
| 2006/0259060 A1 | 11/2006 | Whitson et al. | |
| 2007/0078471 A1 | 4/2007 | Schachar et al. | |
| 2007/0123919 A1 | 5/2007 | Schachar et al. | |
| 2008/0234693 A1 | 9/2008 | Stefanchik | |
| 2009/0157109 A1* | 6/2009 | Bare | A61F 9/0133 606/166 |
| 2013/0041394 A1* | 2/2013 | Ozinga | A61F 9/00736 606/180 |

FOREIGN PATENT DOCUMENTS

| | | |
|---|---|---|
| DE | 2226908 A1 | 12/1972 |
| EP | 0083494 A1 | 7/1983 |
| EP | 1764037 A1 | 3/2007 |
| JP | S61170449 A | 8/1986 |
| JP | 2003530975 A | 10/2003 |
| JP | 2004503276 A | 2/2004 |
| JP | 2004524091 A | 8/2004 |
| JP | 2005237964 A | 9/2005 |
| JP | 2011502575 A | 1/2011 |
| WO | 9403129 A1 | 2/1994 |
| WO | 9418636 A2 | 8/1994 |
| WO | 9842409 A1 | 10/1998 |
| WO | 9917684 A1 | 4/1999 |
| WO | 9917691 A1 | 4/1999 |
| WO | 9930645 A2 | 6/1999 |
| WO | 9930656 A1 | 6/1999 |
| WO | 0074600 A1 | 12/2000 |
| WO | 0145607 A1 | 6/2001 |
| WO | 0195783 A2 | 12/2001 |
| WO | 2005084557 A1 | 9/2005 |

OTHER PUBLICATIONS

Spencer P. Thornton, "Anterior Ciliary Sclerotomy (ACS), A Procedure to Reverse Presbyopia", Surgery for Hyperopia and Presbyopia, 1997, pp. 33-36.

The Surgical Armamentarium (American v. Mueller), 1980, pp. 4, Figure C.

European Search Report dated Sep. 3, 2012 in connection with European Patent Application No. EP 12 17 7148.

Notification of Transmittal of the International Search Report and the Written Opinion of the International Searching Authority, or the Declaration dated Apr. 14, 2009 in connection with PCT Application No. PCT/US2008/081808.

Notification of Transmittal of the International Search Report and the Written Opnion of the International Searching Authority, or the Declaration dated Oct. 22, 2012 in connection with International Patent Application No. PCT/US2012/49986.

Notification of Transmittal of the International Search Report or the Declaration dated Mar. 6, 2008 in PCT Application No. PCT/US03/15896.

International Search Report and Written Opinion of the International Search Authority dated Nov. 5, 2018 in PCT Application No. PCT/US2018/046447.

Office Action dated Apr. 8, 2009 in connection with U.S. Appl. No. 11/606,480.

Office Action dated Dec. 6, 2012 in connection with U.S. Appl. No. 11/606,480.

Office Action dated Dec. 9, 2009 in connection with U.S. Appl. No. 11/698,008.

Office Action dated Feb. 20, 2013 in connection with U.S. Appl. No. 13/205,359.

(56) References Cited

OTHER PUBLICATIONS

Office Action dated Jul. 1, 2009 in connection with U.S. Appl. No. 11/323,284.
Office Action dated Jun. 10, 2010 in connection with U.S. Appl. No. 11/199,591.
Office Action dated Jun. 21, 2011 in connection with U.S. Appl. No. 11/199,591.
Office Action dated May 13, 2009 in connection with U.S. Appl. No. 11/698,008.
Office Action dated May 14, 2013 in connection with U.S. Appl. No. 11/606,480.
Office Action dated Nov. 17, 2009 in connection with U.S. Appl. No. 10/443,122.
Office Action dated Nov. 18, 2011 in connection with U.S. Appl. No. 11/199,591.
Office Action dated Nov. 2, 2009 in connection with US. Appl. No. 11/606,480.
Office Action dated Nov. 25, 2009 in connection with U.S. Appl. No. 11/199,591.
Office Action dated Sep. 22, 2009 in connection with U.S. Appl. No. 11/323,283.
Translation of Office Action dated Dec. 4, 2012 in connection with Japanese Patent Application No. 2010-532244.
Translation of Office Action dated Feb. 8, 2008 in Japanese Patent Application No. 2002-567203.
Translation of Office Action dated Oct. 10, 2015 in Chinese Patent Application No. 201280047325.4.
Translation of Office Action dated Mar. 7, 2016 in Japanese Patent Application No. 2014-525118.

\* cited by examiner

SURGICAL TOOL FOR FORMING INCISIONS IN OCULAR TISSUE WITH TIP PROVIDING VISIBILITY AND RELATED APPARATUS AND METHOD

CROSS-REFERENCE TO RELATED APPLICATION AND PRIORITY CLAIM

This disclosure claims priority under 35 U.S.C. § 119(e) to U.S. Provisional Patent Application No. 62/549,318 filed on Aug. 23, 2017. This provisional application is hereby incorporated by reference in its entirety.

TECHNICAL FIELD

This disclosure is generally directed to surgical devices. More specifically, this disclosure is directed to a surgical tool for forming incisions in ocular tissue with a tip providing visibility and related apparatus and method.

BACKGROUND

Various surgical procedures may be performed on a patient's eye to reduce or correct any number of vision problems. For example, surgical procedures are often performed to treat presbyopia, myopia, hyperopia, elevated intraocular pressure, ocular hypertension, and glaucoma. As a particular example, presbyopia can often be treated by implanting scleral prostheses within the scleral tissue of the patient's eye. For each individual scleral prosthesis, an incision can be made in the sclera of the eye. The incision can then be extended under the surface of the sclera to form a scleral "pocket" or "tunnel," and a scleral prosthesis can be placed within the incision. One or multiple scleral prostheses may be implanted in a patient's eye to partially or completely eliminate presbyopia in the patient's eye. The same or similar technique can also be used to treat glaucoma, ocular hypertension, elevated intraocular pressure, or other eye disorders.

SUMMARY

This disclosure provides a surgical tool for forming incisions in ocular tissue with a tip providing visibility and related apparatus and method.

In a first embodiment, an apparatus includes a footplate configured to receive a surgical blade. The footplate includes a bottom portion configured to rest on ocular tissue of a patient's eye. The bottom portion includes a slot configured to allow passage of a portion of the surgical blade through the bottom portion of the footplate and into the ocular tissue of the patient's eye. The footplate also includes multiple walls having multiple openings. The openings are configured to receive additional portions of the surgical blade such that the surgical blade is rotatable relative to the footplate. The footplate further includes an additional opening or open side configured to allow viewing of the surgical blade and the slot during use.

In a second embodiment, a surgical tool includes a housing having a driver and a surgical blade configured to be bi-directionally rotated by the driver. The surgical tool also includes a footplate configured to receive the surgical blade. The footplate includes a bottom portion configured to rest on ocular tissue of a patient's eye. The bottom portion includes a slot configured to allow passage of a portion of the surgical blade through the bottom portion of the footplate and into the ocular tissue of the patient's eye. The footplate also includes multiple walls having multiple openings. The openings are configured to receive additional portions of the surgical blade such that the surgical blade is rotatable relative to the footplate. The footplate further includes an additional opening or open side configured to allow viewing of the surgical blade and the slot during use.

In a third embodiment, a method includes coupling a surgical blade to a footplate and coupling the footplate to a surgical tool. The footplate includes a bottom portion configured to rest on ocular tissue of a patient's eye. The bottom portion includes a slot configured to allow passage of a portion of the surgical blade through the bottom portion of the footplate and into the ocular tissue of the patient's eye. The footplate also includes multiple walls having multiple openings. The openings are configured to receive additional portions of the surgical blade such that the surgical blade is rotatable relative to the footplate. The footplate further includes an additional opening or open side configured to allow viewing of the surgical blade and the slot during use.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

FIGS. 1 through 10, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, various surgical procedures may be performed on a patient's eye to reduce or correct any number of vision problems, such as when one or more scleral prostheses are implanted in a patient's eye to treat presbyopia or other eye disorders. For each individual scleral prosthesis to be implanted, an incision can be made in the sclera of the eye and extended under the surface of the sclera to form a scleral "pocket" or "tunnel." A scleral prosthesis can then be placed within each of the scleral pockets or tunnels.

In some prior approaches, the implantation of scleral prostheses in a patient's eye has involved the formation of a 360° peritomy of the conjunctiva in the patient's eye. This means that an annular or ring-shaped portion of the conjunctiva was completely removed from the patient's eye, which then allowed the formation of the scleral pockets or tunnels in the sclera of the patient's eye. Unfortunately, the formation of a 360° peritomy in each eye being treated complicated the overall surgical procedure and increased the patient's recovery time.

This disclosure provides a surgical tool for forming incisions in ocular tissue, where a tip of the surgical tool provides improved visibility for an operator or other personnel. Among other things, this improved visibility allows the operator or other personnel to position the surgical tool on a patient's eye so that a surgical blade can pass into scleral tissue of the eye through a small slit or other opening formed in the conjunctiva of the eye. This process forms a scleral pocket or tunnel through the conjunctiva and is therefore referred to as a "trans-conjunctival" procedure. This process can be performed once or multiple times for each of the patient's eyes being treated. In some cases, four scleral pockets or tunnels are formed in the four quadrants of each of the patient's eyes. The one or more small openings formed in the conjunctiva of each eye are much less complicated to form, reducing both the complexity of the surgical procedure and the patient's recovery time.

Figure 1:
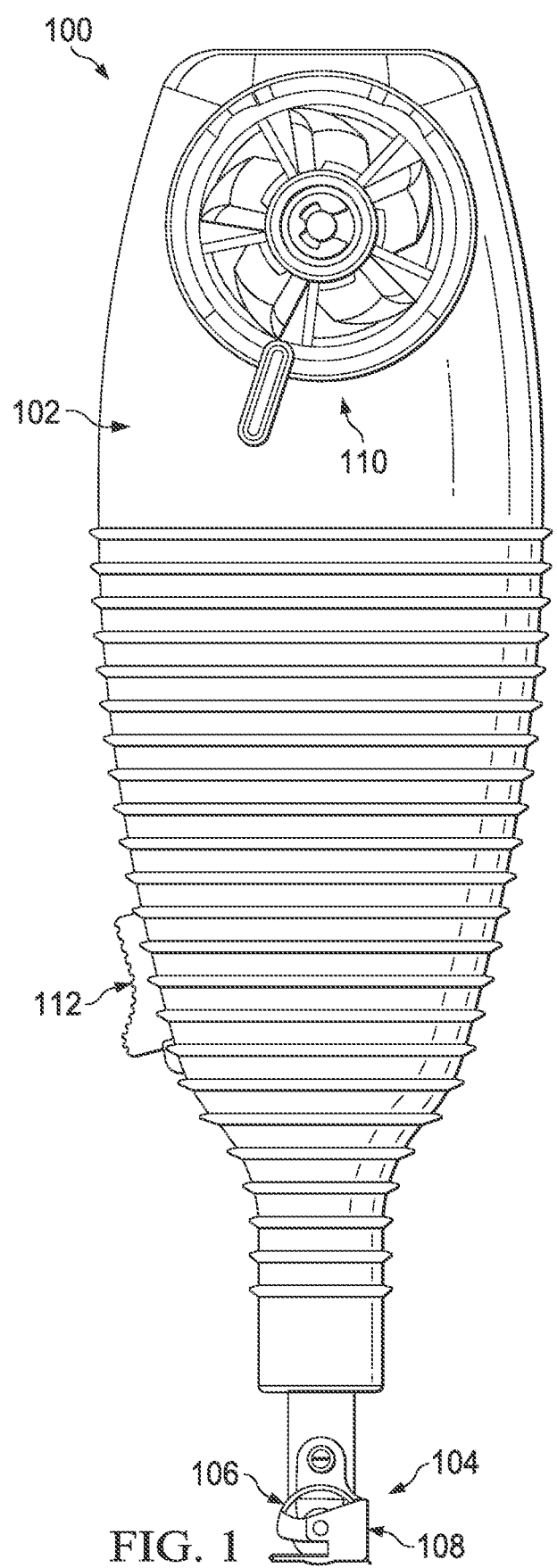
FIGS. 1 and 2 illustrate an example surgical tool for forming incisions in ocular tissue in accordance with this disclosure.
Figure 2:
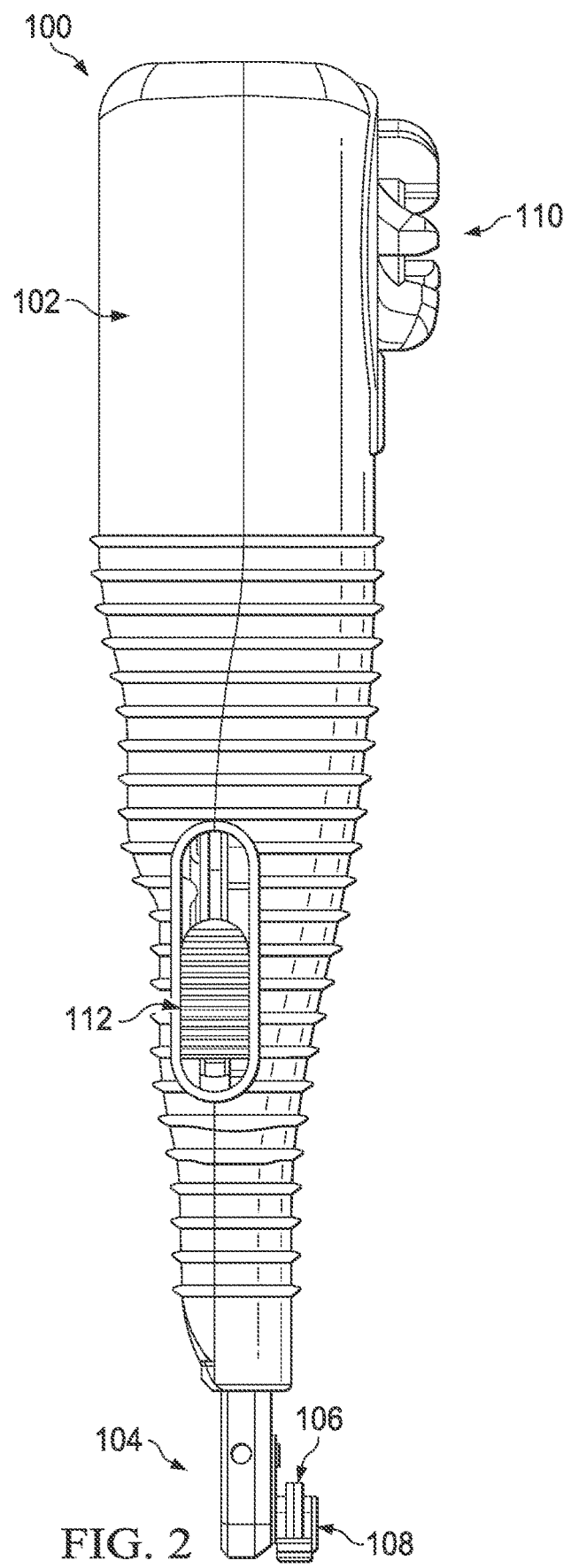

FIGS. 1 and 2 illustrate an example surgical tool 100 for forming incisions in ocular tissue in accordance with this disclosure. As shown in FIGS. 1 and 2, the surgical tool 100 generally includes a housing 102 and a surgical blade assembly 104. The housing 102 generally represents a structure on or in which other components of the surgical tool 100 can be mounted or otherwise placed. Among other things, the housing 102 contains various components that cause rotation of a surgical blade in the surgical blade assembly 104.

The housing 102 includes any suitable structure containing and supporting other components of the surgical tool 100. The housing 102 can be formed from any suitable material or materials, such as metal or plastic. The housing 102 can also have any suitable size, shape, and dimensions, which could vary depending on the layout and arrangement of the other components of the surgical tool 100. In this example, the housing 102 is larger on top and tapers towards the surgical blade assembly 104, and the housing 102 includes ridges or other surface textures in various areas to facilitate secure grasping of the surgical tool 100. However, this is for illustration only, and the housing 102 could have any other suitable form.

The surgical blade assembly 104 includes a surgical blade 106 and a footplate 108. The surgical blade 106 is used to physically form one or more incisions in the ocular tissue of a patient's eye. Rotating the surgical blade 106 in one direction moves a portion of the surgical blade 106 (such as a cutting blade with a sharp tip) into the ocular tissue of the patient's eye. Rotating the surgical blade 106 in the opposite direction moves the portion of the surgical blade 106 out of the ocular tissue of the patient's eye to complete the formation of an incision. The incision itself could have any suitable dimensions based on the size of the surgical blade 106 or a portion thereof. In some embodiments, the surgical blade 106 can form incisions that are approximately four millimeters in length and approximately two to four millimeters in width, although the exact size of the incisions can vary based on a number of factors (such as the size of the scleral prostheses to be inserted into the incisions).

In this way, the surgical blade 106 could be used to, for example, form one or more scleral pockets or scleral tunnels in the scleral tissue of a patient's eye. A scleral pocket generally denotes an incision that is formed at one location on the scleral tissue of a patient's eye and that extends under the surface of the patient's eye for a short distance (meaning there is a single entrance to the scleral pocket on the outside of the patient's eye). A scleral tunnel generally denotes an incision that is formed at one location on the scleral tissue of a patient's eye, that extends under the surface of the patient's eye, and that continues to another location on the scleral tissue of the patient's eye (meaning there are two entrances to the scleral tunnel on the outside of the patient's).

The surgical blade 106 could be formed from any suitable material or materials, such as metal. The surgical blade 106 could be disposable after use (such as per patient or per eye), or the surgical blade 106 could be reusable and formed from material that can withstand a suitable sterilization procedure one or more times. The surgical blade 106 could also be formed in any suitable manner, such as machining, molding, three-dimensional (3D) printing, or other suitable manufacturing technique.

The footplate 108 represents a structure that can be placed on the surface of a patient's eye during use of the surgical tool 100. Once in the proper position, the surgical blade 106 can be rotated, and a portion of the surgical blade 106 passes through the footplate 108 and into the patient's ocular tissue. In some embodiments, the footplate 108 includes one or more slots or other openings that allow the portion of the surgical blade 106 to pass through the footplate 108 and into (and possibly out of) the patient's ocular tissue. Also, in some embodiments, the footplate 108 includes prongs or other mechanisms that help to hold the footplate 108 in position on the patient's eye during use.

The footplate 108 includes any suitable structure facilitating placement of the surgical tool 100 on the patient's eye. The footplate 108 could be formed from any suitable material or materials, such as metal or plastic. The footplate 108 could be disposable after use (such as per patient or per eye), or the footplate 108 could be reusable and formed from material that can withstand a suitable sterilization procedure one or more times. The footplate 108 could also be formed in any suitable manner, such as machining, molding, 3D printing, or other suitable manufacturing technique.

The surgical tool 100 also includes a drive mechanism for causing bi-directional rotation of the surgical blade 106. Any suitable drive mechanism could be used in the surgical tool 100, such as a manual drive mechanism or a motorized/electronic drive mechanism. Example drive mechanisms that could be used in the surgical tool 100 are described in U.S. Pat. Nos. 6,926,727; 8,083,759; and 8,597,318 (which are hereby incorporated by reference in their entirety). As a particular example, a spring-loaded manual drive mechanism could be used (such as is disclosed in U.S. Pat. No. 8,597,318), and the surgical tool 100 includes a winding knob 110 and an activation switch 112 that form a part of the spring-loaded drive mechanism. An operator or other personnel can rotate the winding knob 110 in order to rotate an internal ratchet within the surgical tool 100, causing a spring attached to the ratchet to elongate. An operator or other personnel can then trigger the activation switch 112 to release the ratchet and allow the spring to pull on the ratchet, causing rotation of the ratchet. Rotation of the ratchet causes rotation of the surgical blade 106 and allows the surgical blade 106 to form an incision. In some embodiments, rotation of the winding knob 110 causes the surgical blade 106 to rotate forward and backward a first time, and triggering of the activation switch 112 causes the ratchet to rotate the surgical blade 106 forward and backward a second time. This may allow an operator or other personnel to verify proper operation of the surgical tool 100 when turning the winding knob 110 and allow the surgical tool 100 to form the incision when the activation switch 112 is triggered. Note, however, that any other suitable drive mechanism could be used here.

As described in more detail below, the footplate 108 allows an operator or other personnel to easily view the position and operation of the surgical blade 106. Among other things, this improved visibility is provided by the design of the footplate 108, the way that the surgical blade 106 connects to the footplate 108, and the way that the surgical blade 106 is rotated by the surgical tool. As noted above, this arrangement can be used to support a transconjunctival procedure in which a small slit or other opening is formed in the conjunctiva of a patient's eye so that the tip of the surgical blade 106 can pass through the conjunctival opening into the patient's sclera. This can help to avoid the need for a full 360° peritomy of the conjunctiva, which was previously done to allow for the formation of multiple scleral tunnels.

Although FIGS. 1 and 2 illustrate one example of a surgical tool 100 for forming incisions in ocular tissue, various changes may be made to FIGS. 1 and 2. For example, the surgical tool 100 could have any other suitable form factor, and each component of the surgical tool 100 could have any suitable size, shape, and dimensions. Also, while often described as being used to form scleral pockets or tunnels that receive scleral prostheses to treat presbyopia or other eye disorders, the surgical tool 100 could be used to form any suitable incisions in any suitable tissue for any suitable purpose.

Figure 3:
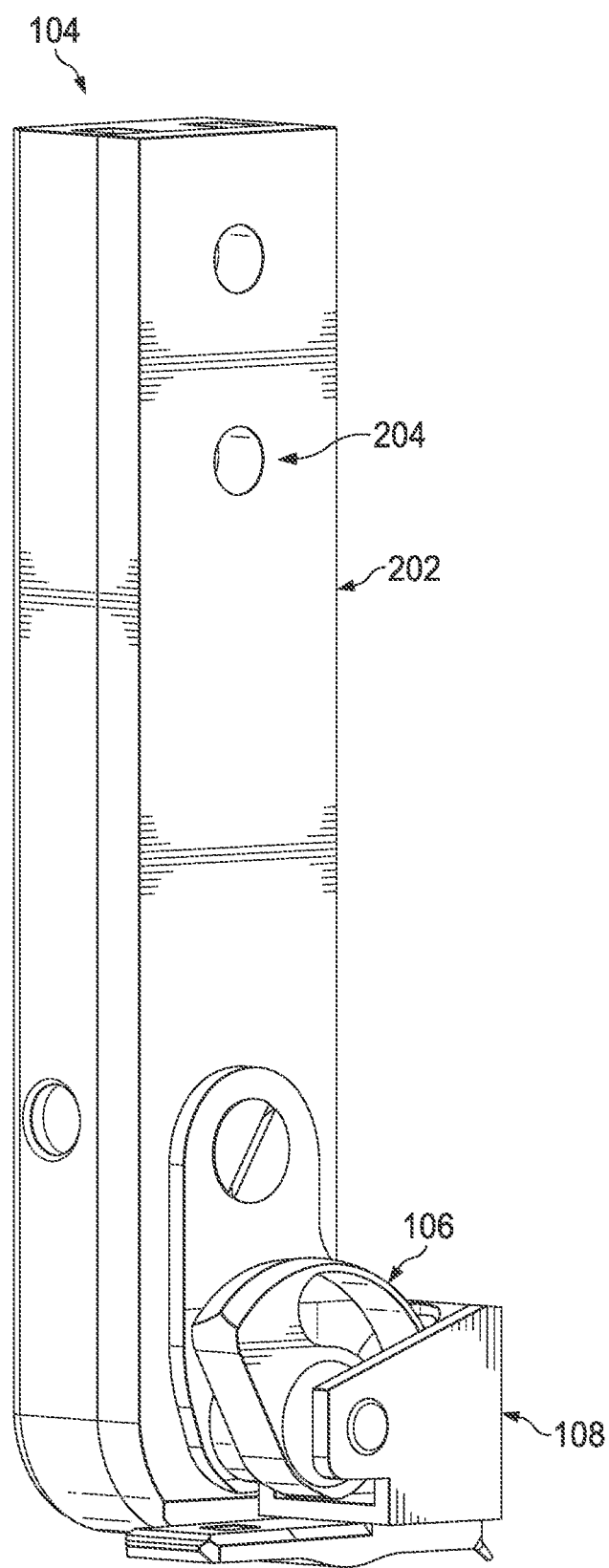
FIGS. 3 and 4 illustrate an example end portion of a surgical tool for forming incisions in ocular tissue in accordance with this disclosure.
Figure 4:
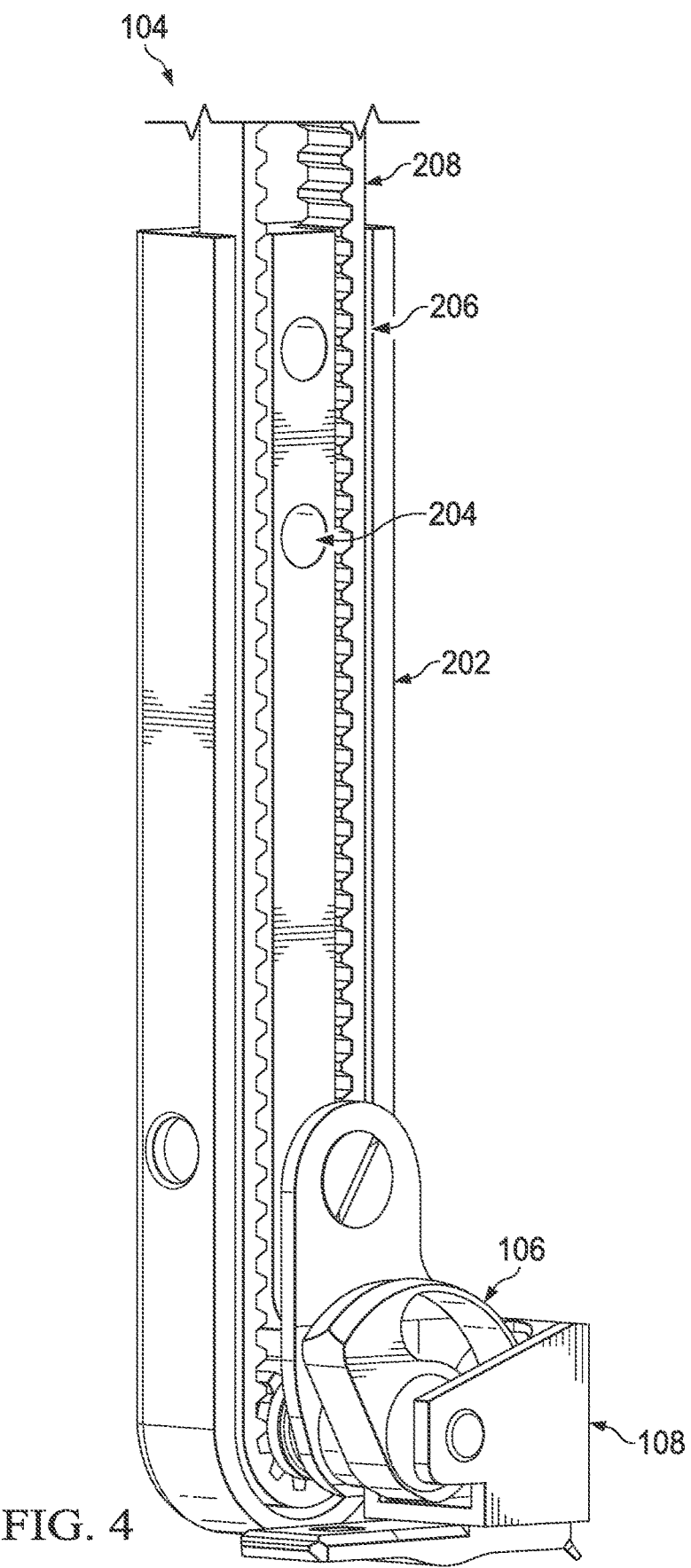

FIGS. 3 and 4 illustrate an example end portion of a surgical tool 100 for forming incisions in ocular tissue in accordance with this disclosure. In particular, FIGS. 3 and 4 illustrate an example of the surgical blade assembly 104 of the surgical tool 100. For ease of explanation, the surgical blade assembly 104 shown in FIGS. 3 and 4 is described as being used with the surgical tool 100 shown in FIGS. 1 and 2. However, the surgical blade assembly 104 could be used with any other suitable surgical tool.

As shown in FIGS. 3 and 4, the surgical blade 106 of the surgical blade assembly 104 is mounted to the footplate 108 of the surgical blade assembly 104. As described in more detail below, the surgical blade 106 can be mounted to the footplate 108 so that the surgical blade 106 is rotatable about its central horizontal axis. This allows the cutting portion of the surgical blade 106 (which is relatively flat in cross-section) to enter into the patient's ocular tissue and form a broad incision. The footplate 108 is also connected to a shaft 202, which can be coupled to the housing 102 via bolts, screws, or other connectors inserted through holes 204 of the shaft 202.

In this example, the shaft 202 is generally straight, but this need not be the case. For example, the shaft 202 could be bent at some point along its length so that the surgical blade assembly 104 is not aligned vertically with the housing 102, or the shaft 202 could be straight but could extend from the housing 102 at an angle. In other words, at least the portion of the shaft 202 coupled to the surgical blade assembly 104 (and possibly the entire shaft 202) could be at an oblique angle with respect to the housing 102.

As shown in FIG. 4, a portion of the shaft 202 has been removed to reveal a channel 206 within the shaft 202. The channel 206 travels from the top of the shaft 202 under a gear connected to the surgical blade 106 and back to the top of the shaft 202. The channel 206 allows a drive belt 208 to be placed through the shaft 202 and next to the gear connected to the surgical blade 106. The drive belt 208 is also coupled to the drive mechanism of the surgical tool 100.

The drive belt 208 can be rotated bi-directionally by the drive mechanism of the surgical tool 100 in order to impart bi-directional rotation to the surgical blade 106. For example, rotation of the drive belt 208 in one direction (clockwise in this example) can cause a portion of the surgical blade 106 to enter into the ocular tissue of the patient's eye. Rotation of the drive belt 208 in the opposite direction (counter-clockwise in this example) can cause the portion of the surgical blade 106 to move out of the ocular tissue of the patient's eye and complete the formation of an incision in the patient's ocular tissue.

The shaft 202 could be formed from any suitable material or materials, such as metal or plastic. The shaft 202 can be formed from material that can withstand a suitable sterilization procedure one or more times. The shaft 202 could also be formed in any suitable manner, such as machining, molding, 3D printing, or other suitable manufacturing technique. The holes 204 in the shaft 202 could be formed in any suitable manner, such as by machining the shaft 202 to form the holes 204 or forming the shaft 202 to include the holes 204. The channel 206 could have any suitable size, shape, and dimensions and be formed in any suitable manner. In some embodiments, the shaft 202 could be formed in multiple pieces, such as those where one piece of the shaft 202 includes the channel 206 and another piece of the shaft 202 covers the channel 206. However, other embodiments of the shaft 202 and the channel 206 could be used, including those having a shaft 202 formed in an integral manner.

Although FIGS. 3 and 4 illustrate one example of an end portion of a surgical tool 100 for forming incisions in ocular tissue, various changes may be made to FIGS. 3 and 4. For example, the surgical blade assembly 104 could have any other suitable form factor, and each component of the surgical blade assembly 104 could have any suitable size, shape, and dimensions.

Figure 5:
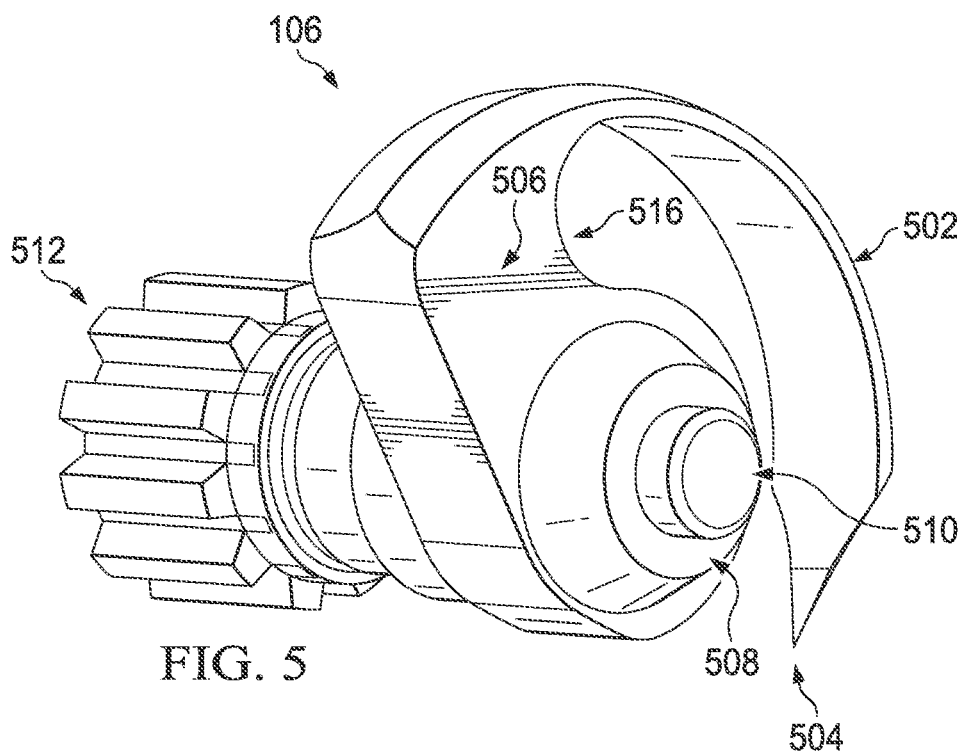
FIGS. 5 and 6 illustrate an example surgical blade used in a surgical tool for forming incisions in ocular tissue in accordance with this disclosure.
Figure 6:
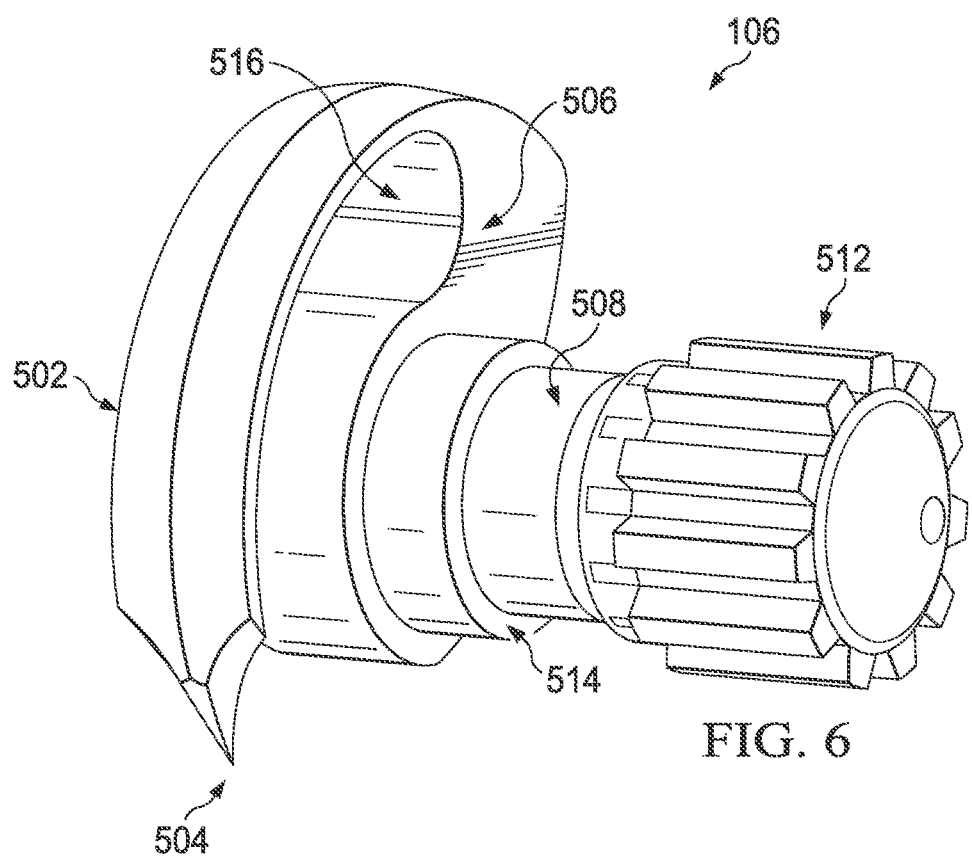

FIGS. 5 and 6 illustrate an example surgical blade 106 used in a surgical tool 100 for forming incisions in ocular tissue in accordance with this disclosure. For ease of explanation, the surgical blade 106 shown in FIGS. 5 and 6 is described as being used in the surgical blade assembly 104 shown in FIGS. 3 and 4 with the surgical tool 100 shown in FIGS. 1 and 2. However, the surgical blade 106 could be used with any other suitable surgical blade assembly and any other suitable surgical tool.

As shown in FIGS. 5 and 6, the surgical blade 106 includes a cutting blade 502 that terminates in a sharp tip 504, a connecting arm 506, and a central portion 508. The cutting blade 502 is curved and arches circumferentially around a central horizontal axis of the surgical blade 106, where the central horizontal axis is located at the center of the central portion 508). The tip 504 of the cutting blade 502 can form an incision through ocular tissue of a patient's eye. In this example, the sides of the tip 504 are somewhat curved so that the tip 504 is more pronounced. Note, however, that the tip 504 could have other suitable forms, such as tips that include straight sides. The connecting arm 506 couples the cutting blade 502 to the central portion 508 of the surgical blade 106. The central portion 508 of the surgical blade 106 can be rotated by the surgical tool 100, and rotation of the central portion 508 of the surgical blade 106 results in movement of the cutting blade 502 via the physical connection between the central portion 508 and the cutting blade 502 formed by the connecting arm 506.

By rotating the central portion 508 of the surgical blade 106 in one direction (clockwise in FIG. 5 and counter-clockwise in FIG. 6), the cutting blade 502 can be moved into ocular tissue of a patient's eye and form an incision, such as a scleral pocket or a scleral tunnel. The sharp tip 504 of the cutting blade 502 helps to ensure that a clean incision is formed in the patient's ocular tissue. By rotating the central portion 508 of the surgical blade 106 in the opposite direction (counter-clockwise in FIG. 5 and clockwise in FIG. 6), the cutting blade 502 can be retracted from the ocular tissue of the patient's eye. This completes the formation of the incision in the patient's eye.

In this example, the cutting blade 502 is curved, which could help to form incisions that extend under the outer surface of a patient's eye. For example, rotating the cutting blade 502 clockwise in FIG. 5 allows the tip 504 of the cutting blade 502 to enter into the patient's ocular tissue at one location. Continued rotation of the cutting blade 502 allows the tip 504 of the cutting blade 502 to travel some distance underneath the surface of the patient's ocular tissue. If the cutting blade 502 is retracted at that point, a scleral pocket is formed. Additional rotation of the cutting blade 502 allows the tip 504 of the cutting blade 502 to exit the patient's ocular tissue at a position spaced apart from where the tip 504 of the cutting blade 502 entered the patient's ocular tissue. At that point, a scleral tunnel is formed. In either case, the cutting blade 502 ideally remains solely within the scleral tissue of a patient's eye, helping to ensure that the patient's sclera is not perforated during the procedure.

Note, however, that the surgical blade 106 could be used to form any other suitable incision, and the surgical blade 106 could use any suitable type of cutting blade (curved or otherwise). Also, in some embodiments, the surgical blade 106 could be replaceable so that the surgical tool 100 can be reused for multiple patients. In other embodiments, the surgical tool 100 itself could be disposable, and the surgical blade 106 may or may not be removable.

As can be seen here, one side of the surgical blade 106 includes a projection 510, and the opposite side of the surgical blade 106 includes or is coupled to a gear 512. In some embodiments, the surgical blade 106 is removably coupled to the gear 512. This allows the gear 512 to be attached to the surgical blade 106 after the surgical blade 106 is inserted into or otherwise mounted to the footplate 108.

The projection 510 can be inserted into a corresponding opening of the footplate 108 to help secure the surgical blade 106 in place while allowing rotation of the surgical blade 106. A raised lip 514 located on the central portion 508 can also engage the footplate 108 along a side of the footplate 108 opposite the side in which the projection 510 is inserted. Collectively, the projection 510 and the raised lip 514 help to maintain the position of the surgical blade 106 within the footplate 108. The gear 512 can engage a drive belt 208 of the surgical tool 100, which as noted above can be inserted into the channel 206 of the shaft 202. Thus, the gear 512 can also be inserted into the shaft 202 in order to engage the drive belt 208. However, other drive mechanisms could also be used to drive the surgical blade 106.

The drive belt 208 can be rotated by the drive mechanism in the upper portion or other portion of the housing 102, and the drive belt 208 can cause rotation of the surgical blade 106 through contact with the gear 512. The size of the gear 512 here can control how rapidly the surgical blade 106 rotates in response to movement of the drive belt 208. For instance, a smaller gear 512 would rotate the surgical blade 106 faster compared to a larger gear 512 given the same amount of movement by the drive belt 208. The size of the gear 512 can therefore be selected in order to achieve the desired level of speed when operating the surgical tool 100 to form the incisions.

It should be noted that while a gear 512 is shown here, other mechanisms could be used to couple rotation of a drive belt with rotation of the surgical blade 106. For example, the drive belt 208 could represent a flat or tape-like belt that engages a cylindrical axle of the surgical blade 106 to produce rotation of the surgical blade 106 through frictional contact with the surgical blade's axle. As another example, the central portion 508 of the surgical blade 106 could be physically attached to a particular location of the drive belt 208 so that rotation of the drive belt 208 physically pulls or pushes the central portion 508 of the surgical blade 106. In general, any suitable mechanism can be used here to cause rotation of the surgical blade 106.

A portion of the connecting arm 506 in this example can function as a hard stop 516. During operation, the maximum amount that the surgical blade 106 can be rotated is defined by the point where the hard stop 516 contacts part of the footplate 108. At that point, rotation of the surgical blade 106 into the patient's ocular tissue cannot proceed further. The length of the cutting blade 502 from the hard stop 516 can control the size and type of incisions being formed, such as when a shorter cutting blade 502 is used to form scleral pockets and a longer cutting blade 502 is used to form scleral tunnels. In some embodiments, however, the hard stop 516 functions only as a safety mechanism to prevent over-rotation of the surgical blade 106, and the drive mechanism of the surgical tool 100 could normally operate to rotate the surgical blade 106 without causing the hard stop 516 to actually contact the footplate 108.

Although FIGS. 5 and 6 illustrate one example of a surgical blade 106 used in a surgical tool 100 for forming incisions in ocular tissue, various changes may be made to FIGS. 5 and 6. For example, the surgical blade 106 could have any other suitable form factor, and each component of the surgical blade 106 could have any suitable size, shape, and dimensions. Also, the surgical blade 106 could be driven in other ways and may or may not include a gear.

Figure 7:
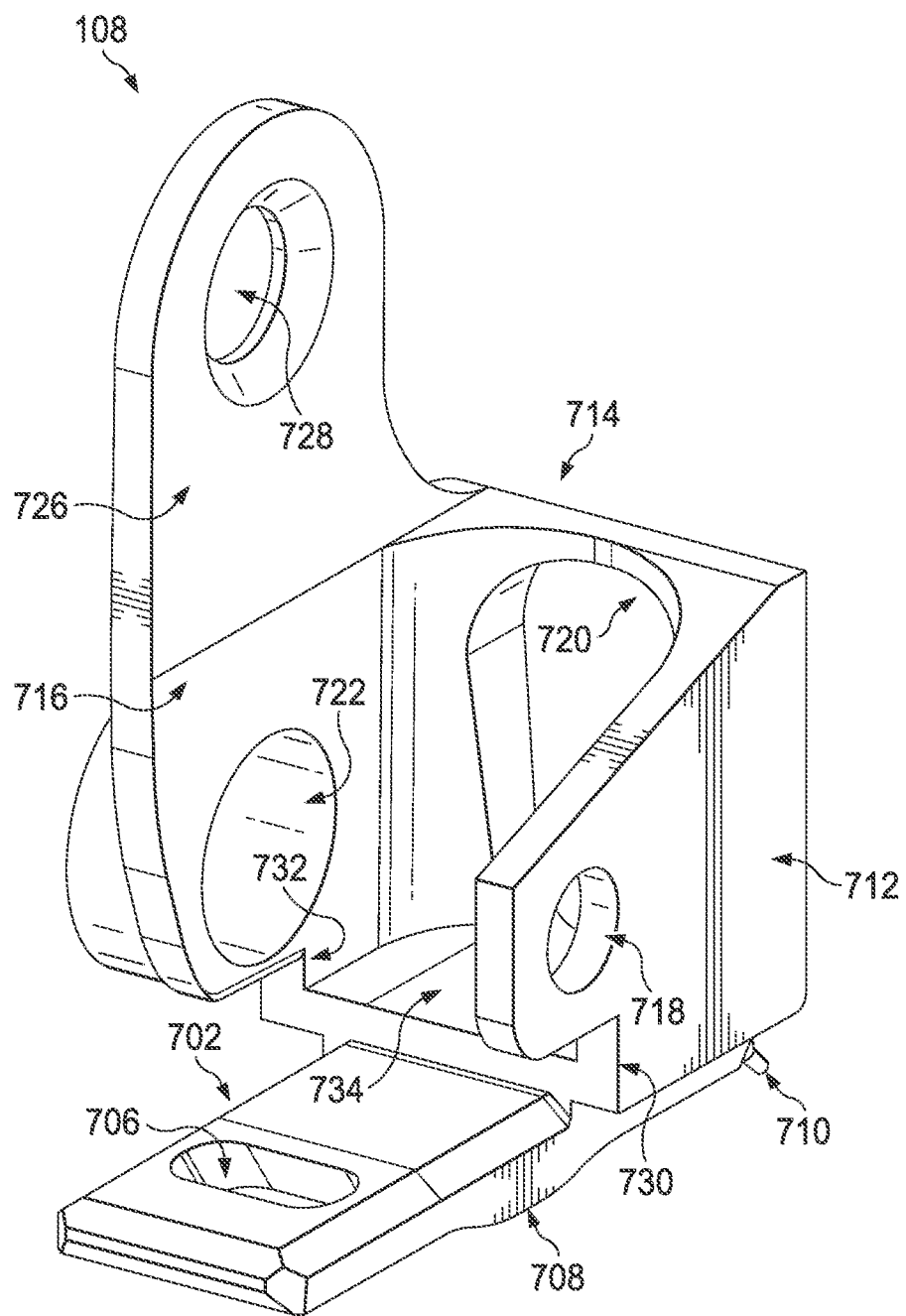
FIGS. 7 through 9 illustrate an example footplate used in a surgical tool for forming incisions in ocular tissue in accordance with this disclosure.
Figure 8:
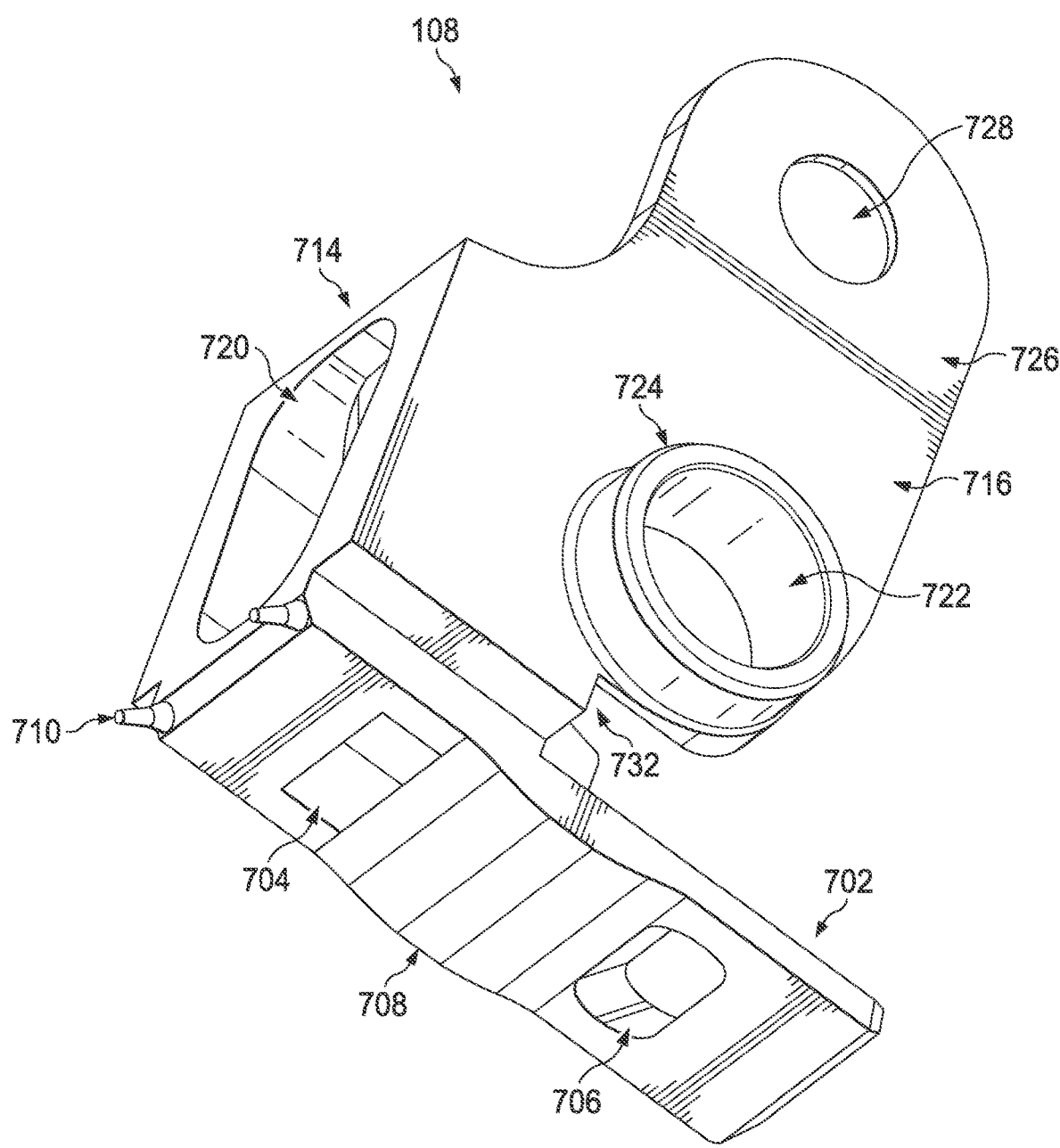
Figure 9:
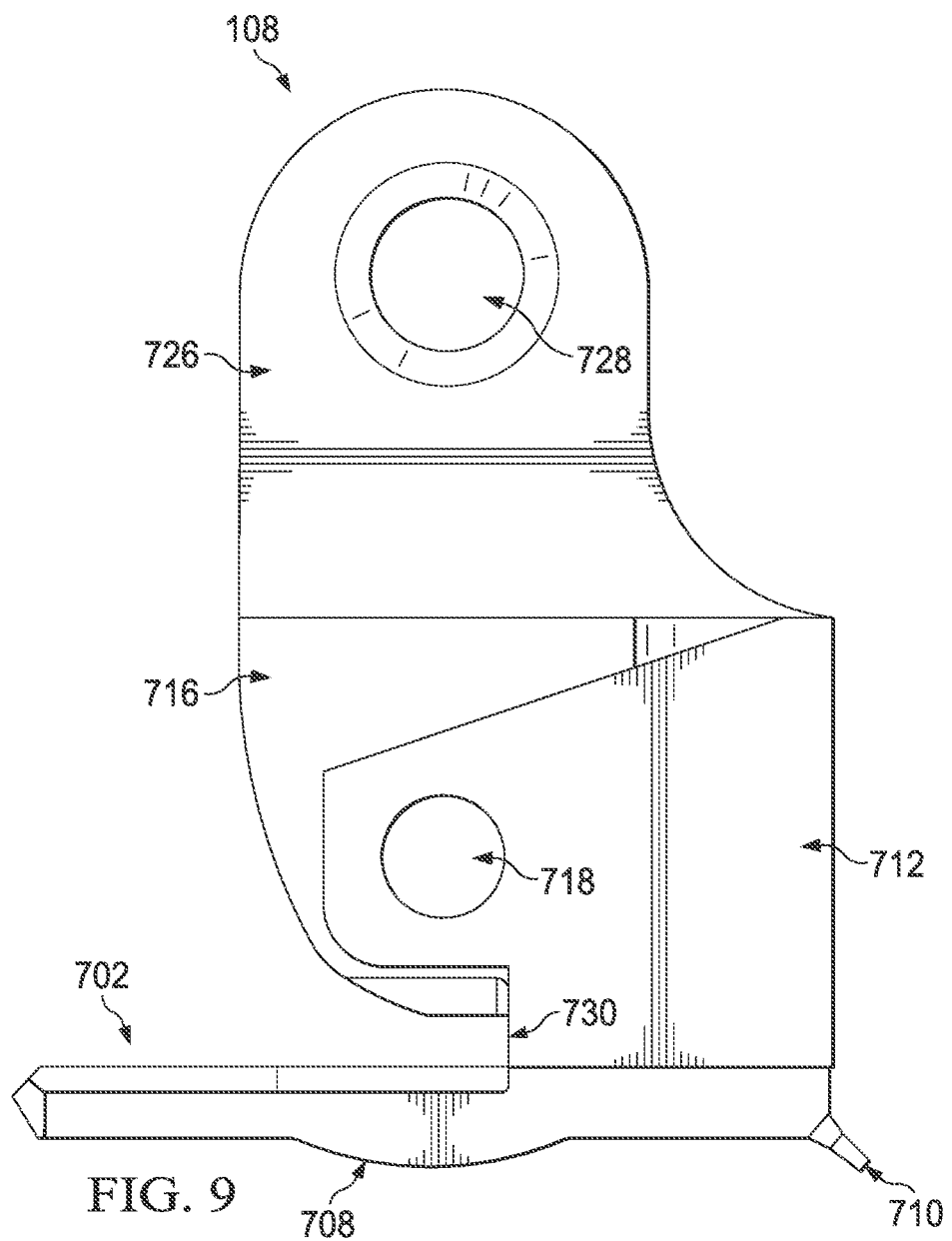

FIGS. 7 through 9 illustrate an example footplate 108 used in a surgical tool for forming incisions in ocular tissue in accordance with this disclosure. For ease of explanation, the footplate 108 shown in FIGS. 7 through 9 is described as being used in the surgical blade assembly 104 shown in FIGS. 3 and 4 with the surgical blade 106 shown in FIGS. 5 and 6 in the surgical tool 100 shown in FIGS. 1 and 2. However, the footplate 108 could be used with any other suitable surgical blade assembly, any other suitable surgical blade, and any other suitable surgical tool.

As shown in FIGS. 7 through 9, the footplate 108 includes a bottom portion 702 having two slots or other openings 704 and 706. In this example, each opening 704 and 706 is generally elongated, where one opening 704 has squared ends or corners and the other opening 706 has rounded ends or corners. However, other forms for the openings 704 and 706 could be used here, and the openings 704 and 706 may or may not have similar forms. Also, the opening 704 appears to be formed straight through the bottom portion 702 of the footplate 108 here, while the opening 706 appears to be formed diagonally through the bottom portion 702 of the footplate 108 here. However, the opening 706 could be formed straight through the bottom portion 702 of the footplate 108, or the opening 704 could be formed diagonally through the bottom portion 702 of the footplate 108.

The use of one or more diagonal openings 704 and 706 through the bottom portion 702 of the footplate 108 may provide a more contoured passage for the curved cutting blade 502 to pass through the bottom portion 702 of the footplate 108.

The bottom portion 702 of the footplate 108 can be placed on the outer surface of a patient's eye, and the tip 504 of the surgical blade 106 can pass through the opening 704 into the patient's ocular tissue. Depending on the incision being formed, the tip 504 of the surgical blade 106 can also pass out of the patient's ocular tissue and through the opening 706. Note that while two openings 704 and 706 are shown here, a single opening 704 or 706 could also be used, such as when the surgical tool 100 is used to form scleral pockets but not scleral tunnels. Also note that the orientation of the surgical blade 106 can be reversed so that the tip 504 of the surgical blade 106 can pass through the opening 706 into the patient's ocular tissue and possibly out of the patient's ocular tissue and through the opening 704.

The bottom portion 702 of the footplate 108 also includes a convex bottom surface 708 and one or more prongs 710. The convex bottom surface 708 is located between the openings 704 and 706 and in a central area of the bottom portion 702. The convex bottom surface 708 operates to compress ocular tissue under the footplate 108 when the footplate 108 is placed on a patient's eye. The cutting blade 502 could then pass through the compressed ocular tissue to form an incision. The compression of the ocular tissue in this manner allows the surgical blade 106 to be used to form incisions of more consistent depth in patients' eyes. In some embodiments, for example, the convex bottom surface 708 can help to ensure that the incisions in the patients' eyes are more consistently formed about 400 microns to about 450 microns in depth in the patients' eyes. However, other depths could also be obtained using the surgical tool 100. Also, it is possible when using the surgical tool 100 that the depths may not be particularly consistent within each eye, across the same patient's eyes, or across different patients' eyes.

The prongs 710 can be placed against (and possibly into) the patient's ocular tissue in order to help hold the surgical tool 100 in place during use. The prongs 710 could have any suitable size and shape. Also, any number of prongs 710 could be used in any suitable location(s) and have any suitable orientation(s) on the bottom portion 702 or one or more sides of the footplate 108. In this example, there are two prongs 710 extending from two bottom corners of the footplate 108. Also, each prong 710 extends in a substantially straight direction, and the two prongs 710 are generally parallel to each other. However, other numbers and orientations of the prongs 710 could be used. As another example, two prongs 710 could be used in the same positions as shown here, but the prongs 710 could angle away from one another.

The footplate 108 further includes three walls 712, 714, and 716 that partially box in (partially enclose) a space where the surgical blade 106 is located or inserted. Note that while three distinct walls 712, 714, and 716 are shown here, other arrangements could be used here. For example, curved portions could join the walls 712, 714, and 716. In some embodiments, this could create the appearance that the walls 712, 714, and 716 form a single U-shaped wall or other curved wall.

The wall 712 includes an opening 718 that is configured to receive the projection 510 of the surgical blade 106. Since the projection 510 and the opening 718 are both generally circular or cylindrical, the surgical blade 106 is able to rotate after insertion of the projection 510 into the opening 718.

The wall 714 includes an opening 720, which could allow an operator or other personnel to view the position/status of the surgical blade 106. For example, the operator or other personnel could view the cutting blade 502 through the opening 720 in order to properly align the tip 504 with a desired starting point for an incision. The operator or other personnel could also view the cutting blade 502 through the opening 720 in order to monitor rotation of the surgical blade 106 and ensure that the tip 504 of the cutting blade 502 has exited the patient's ocular tissue before the surgical tool 100 is moved. In this example, the opening 720 is wider near the top of the wall 714 and narrower near the bottom of the wall 714. However, this is for illustration only, and the opening 720 could have any other suitable form allowing an operator or other personnel to view the interior space partially enclosed by the walls 712, 714, and 716. It is also possible for multiple smaller openings 720 to be formed in the wall 714.

The wall 716 includes an opening 722 that allows the gear 512 to be coupled to the surgical blade 106 through the wall 716. For example, in some embodiments, part of the central portion 508 of the surgical blade 106 could be inserted through the opening 722, and the gear 512 could then be coupled to the central portion 508 of the surgical blade 106. In other embodiments, part of the central portion 508 of the surgical blade 106 could be coupled to the gear 512, and that part of the central portion 508 of the surgical blade 106 could be inserted through the opening 722 and connected to another portion of the surgical blade 106. Note that these are only examples of how the surgical blade 106 could be assembled or mounted in the footplate 108. There are various other ways in which the surgical blade 106 could be formed using multiple components that are then assembled within the footplate 108 or otherwise mounted in the footplate 108.

In this example, a rim 724 is located around the opening 722. The rim 724 could fit within a hole in the shaft 202, which can help to maintain the gear 512 within the shaft 202 so that the gear 512 is able to effectively engage the drive belt 208 within the channel 206 of the shaft 202. Here, the raised lip 514 on the central portion 508 of the surgical blade 106 can contact the inner surface of the wall 716 around the opening 722. This in combination with the projection 510 being inserted into the opening 718 of the wall 712 helps to hold the surgical blade 106 in place within the partially enclosed space defined by the walls 712, 714, and 716 of the footplate 108. The rim 724 also helps to prevent the gear 512 (once attached to the central portion 508 of the surgical blade 106) from moving inward towards the interior of the partially enclosed space defined by the walls 712, 714, and 716 during use. If the gear 512 was allowed to move inward like this, it might result in the application of enough force to move the surgical blade 106 within the partially enclosed space defined by the walls 712, 714, and 716.

A flange 726 extends from the wall 716 and includes an opening 728. The opening 728 allows a bolt, screw, or other connector to pass through the flange 726 and attach the footplate 108 to the shaft 202 of the surgical tool 100 (as shown in FIGS. 3 and 4). The presence of the connector through the opening 728 and the insertion of the rim 724 into the shaft 202 can help prevent rotation of the entire footplate 108 during use. Note that while the flange 726 is shown here as having various curved sides defining its shape, the flange 726 could have any suitable size and shape.

In this example, the walls 712 and 714 here are shown as including notches 730 and 732, respectively. The notches 730 and 732 are respectively located at least partially under the openings 718 and 722 in the walls 712 and 714. These notches 730 and 732 help to provide additional viewing areas where portions of the surgical blade 106 can be seen by an operator or other personnel. Note, however, that the use of the notches 730 and 732 is not necessarily required. Also, the notches 730 and 732 are shown here as including generally squared corners, although other forms for the notches 730 and 732 could be used (and the notches 730 and 732 could have different forms).

As can be seen here, a bottom wall 734 could be used here to connect the walls 712, 714, and 716 to the bottom portion 702 of the footplate 108. In this example, the bottom wall 734 is wider than the bottom portion 702, which allows the walls 712, 714, and 716 to define a space for the surgical blade 106 that is as wide as or wider than the bottom portion 702 of the footplate 108. However, this need not be the case. In other embodiments, for example, the walls 712, 714, and 716 could be connected directly to the bottom portion 702 of the footplate 108. Also, while the bottom wall 734 is aligned with one shorter edge of the bottom portion 702 of the footplate 108 as seen in FIG. 8, the bottom wall 734 could extend beyond the shorter edge of the bottom portion 702 of the footplate 108.

The footplate 108 can be used as described above to compress underlying ocular tissue in order to help the surgical blade 106 form incisions with more consistent depths in patients' eyes. The design of the footplate 108 also allows the surgical blade 106 and the openings 704 and 706 of the footplate 108 to be easily viewable to an operator or other personnel. This is because the surgical blade 106 is not completely enclosed in walls and the wall 714 includes the large opening 720.

Because of this, an opening can be formed in the conjunctiva of a patient's eye, and the surgical tool 100 can be positioned so that the tip 504 of the surgical blade 106 will pass through the conjunctival opening and into the patient's scleral tissue. This can be done in multiple locations (such as approximately 45°, 135°, 225°, and 315°) on the patient's eye to form four scleral pockets or tunnels that can receive four scleral prostheses. Example scleral prostheses that could be inserted into patients' eyes are disclosed in U.S. Pat. Nos. 8,409,277 and 8,911,496 (which are hereby incorporated by reference in their entirety). Other example scleral prostheses that could be inserted into patients' eyes are disclosed in U.S. Pat. Nos. 6,007,578; 6,280,468; 6,991,650; and 7,785,367 (which are hereby incorporated by reference in their entirety). Other scleral prostheses or implants could also be used and inserted into the incisions formed using the surgical tool 100 as described above.

As can be seen here, there is no need to perform a full 360° peritomy of the conjunctiva in order to completely remove the conjunctiva from the areas where the incisions are to be formed. This helps to simplify the medical procedure and decrease patients' recovery times, two factors that are extremely important in ocular surgeries.

Although FIGS. 7 through 9 illustrate one example of a footplate 108 used in a surgical tool for forming incisions in ocular tissue, various changes may be made to FIGS. 7 through 9. For example, the footplate 108 could have any other suitable form factor, and each component of the footplate 108 could have any suitable size, shape, and dimensions. Also, various features or components of the footplate 108 could be omitted as needed or desired, such as when only one opening 704 or 706 is provided in a surgical tool 100 used to form scleral pockets (and not scleral tunnels).

Figure 10:
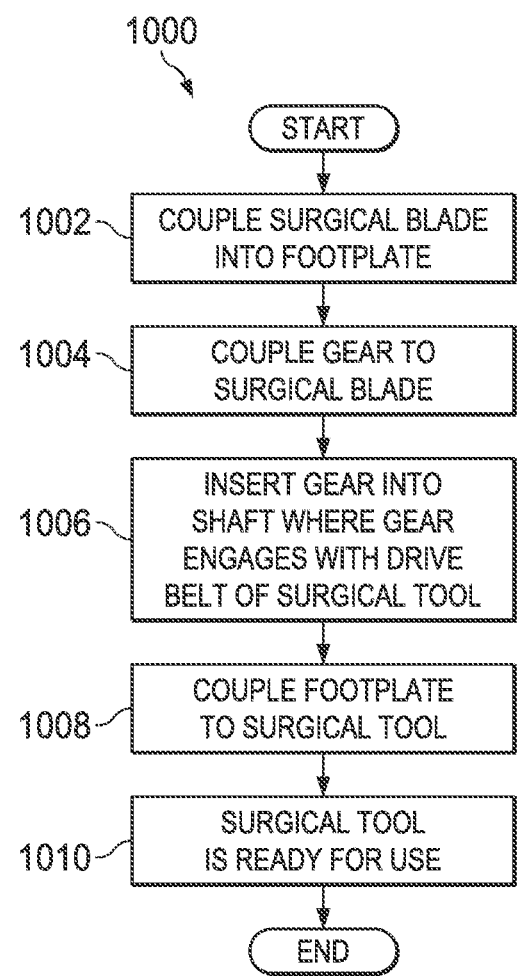
FIG. 10 illustrates an example method for preparing a surgical tool for use in forming incisions in ocular tissue in accordance with this disclosure.

FIG. 10 illustrates an example method 1000 for preparing a surgical tool for use in forming incisions in ocular tissue in accordance with this disclosure. For ease of explanation, the method 1000 is described as being performed using the surgical tool 100 of FIGS. 1 and 2 with the surgical blade assembly 104 of FIGS. 3 and 4, the surgical blade 106 of FIGS. 5 and 6, and the footplate 108 of FIGS. 7 through 9. However, the method 1000 could involve the use of any suitable surgical tool having any suitable surgical blade assembly, any suitable surgical blade, and any suitable footplate.

As shown in FIG. 10, a surgical blade is coupled to a footplate at step 1002, and a gear is coupled to the surgical blade at step 1004. This could include, for example, an operator or other personnel inserting the projection 510 of the surgical blade 106 into the opening 718 of the footplate 108. In some embodiments, this could also include the operator or other personnel inserting part of the central portion 508 of the surgical blade 106 through the opening 722 of the footplate 108 and connecting the gear 512 to that part of the central portion 508. In other embodiments, this could also include the operator or other personnel inserting part of the central portion 508 of the surgical blade 106 with the gear 512 already attached through the opening 722 of the footplate 108 and connecting that part of the central portion 508 to another part of the surgical blade 106. As noted above, there are different ways in which various components could be used here to mount a surgical blade 106 to a footplate 108.

The gear is inserted into a shaft of a surgical tool at step 1006, and the footplate is coupled to the surgical tool at step 1008. This could include, for example, the operator or other personnel inserting the gear 512 through an opening of the shaft 202 so that the gear 512 is able to engage a drive belt 208 that has been or will be inserted through the channel 206 of the shaft 202. This could also include the operator or other personnel inserting the rim 724 of the footplate 108 into the opening of the shaft 202. This could further include the operator or other personnel inserting a bolt, screw, or other connector through the opening 728 of the footplate 108 into a corresponding opening of the shaft 202 and tightening the connector. Ideally, this secures the footplate 108 to the surgical tool 100 and prevents rotation of the footplate 108.

At this point, the surgical tool is ready to be used at step 1010. An operator or other personnel could use the surgical tool in any suitable manner at this point. For example, after a surgeon or other personnel has formed one or more openings in the conjunctiva of a patient's eye, the surgeon or other personnel could wind the knob 110 and maneuver the surgical tool 100 so that the sharp tip 504 is positioned to enter the patient's ocular tissue through one opening in the patient's conjunctiva. This can be done since the footplate 108 offers improved visibility of the openings 704 and 706 and the surgical blade 106, such as through the opening 720 in the wall 714 of the footplate 108. The surgeon or other personnel could use the prongs 710 of the footplate 108 to help hold the footplate 108 in a desired position on the patient's eye, and the surgeon or other personnel could press the surgical tool 100 down onto the patient's eye so that the convex bottom surface 708 of the footplate 108 compresses the patient's ocular tissue. Once ready, the surgeon or other personnel can trigger the activation switch 112, causing the surgical blade 106 to rotate in one direction. The tip 504 of the cutting blade 502 can pass through one of the openings 704 and 706 into the patient's ocular tissue, pass some distance through the patient's ocular tissue, and optionally exit the patient's ocular tissue and pass through another of the openings 704 and 706. The surgical blade 106 then rotates in the opposite direction to remove the cutting blade 502 from the patient's ocular tissue. This process can be repeated any suitable number of times to form any suitable number of incisions in the patient's ocular tissue. Of course, as noted above, other uses for the surgical tool 100 are also possible.

Although FIG. 10 illustrates one example of a method 1000 for preparing a surgical tool for use in forming incisions in ocular tissue, various changes may be made to FIG. 10. For example, while shown as a series of steps, various steps in FIG. 10 could overlap, occur in parallel, occur in a different order, or occur any number of times. Also, as noted above, the use of a gear is optional, and other mechanisms could be used to support rotation of a surgical blade.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
 a footplate configured to receive a surgical blade, the footplate comprising:
  a bottom portion configured to rest on ocular tissue of a patient's eye, the bottom portion comprising a slot configured to allow passage of a portion of the surgical blade through the bottom portion of the footplate and into the ocular tissue of the patient's eye;
  first and second walls located along opposite sides of the footplate, the first wall comprising a first opening, the second wall comprising a second opening, the first opening configured to receive a projection from the surgical blade and the second opening configured to receive a central portion of the surgical blade that includes or is coupled to a gear such that the surgical blade is rotatable relative to the footplate; and
  an additional opening or open side configured to allow viewing of the surgical blade and the slot during use.

2. The apparatus of claim 1, wherein the bottom portion comprises a convex bottom surface configured to contact and compress the ocular tissue of the patient's eye.

3. The apparatus of claim 1, wherein the footplate further comprises:
 a third wall comprising the additional opening, the third wall extending between the first and second walls.

4. The apparatus of claim 3, wherein the footplate lacks a wall opposite the third wall.

5. The apparatus of claim 1, wherein the footplate further comprises:
 a flange extending from the second wall, the flange comprising a third opening configured to receive a connector that couples the footplate to a surgical tool.

6. The apparatus of claim 1, wherein the bottom portion further comprises a second slot configured to allow passage of at least a tip of the surgical blade through the bottom portion of the footplate.

7. The apparatus of claim 1, wherein the gear is configured to be inserted into a shaft of a surgical tool and engage a drive belt within the shaft of the surgical tool.

8. A surgical tool comprising:
 a housing comprising a driver;
 a surgical blade configured to be bi-directionally rotated by the driver; and
 a footplate configured to receive the surgical blade, the footplate comprising:
  a bottom portion configured to rest on ocular tissue of a patient's eye, the bottom portion comprising a slot configured to allow passage of a portion of the surgical blade through the bottom portion of the footplate and into the ocular tissue of the patient's eye;
  first and second walls located along opposite sides of the footplate, the first wall comprising a first opening, the second wall comprising a second opening, the first opening configured to receive a projection from the surgical blade and the second opening configured to receive a central portion of the surgical blade that includes or is coupled to a gear such that the surgical blade is rotatable relative to the footplate; and
  an additional opening or open side configured to allow viewing of the surgical blade and the slot during use.

9. The surgical tool of claim 8, wherein the bottom portion comprises a convex bottom surface configured to contact and compress the ocular tissue of the patient's eye.

10. The surgical tool of claim 8, wherein the gear is configured to be inserted into a shaft of the surgical tool and engage a drive belt within the shaft of the surgical tool.

11. The surgical tool of claim 8, wherein the footplate further comprises:

a third wall comprising the additional opening, the third wall extending between the first and second walls.

12. The surgical tool of claim 11, wherein the footplate lacks a wall opposite the third wall.

13. The surgical tool of claim 8, wherein the footplate further comprises:
a flange extending from the second wall, the flange comprising a third opening configured to receive a connector that couples the footplate to the surgical tool.

14. The surgical tool of claim 8, wherein the driver comprises:
a knob configured to be turned by an operator to prepare the surgical tool for use; and
a switch configured to be activated by the operator to trigger bidirectional rotation of the surgical blade.

15. The surgical tool of claim 8, wherein the surgical blade comprises:
the central portion;
a connecting arm coupled to the central portion; and
a cutting blade coupled to the connecting arm and arching around an axis through the central portion; and
wherein the central portion of the surgical blade includes or is configured to be coupled to the gear, the gear configured to engage a drive belt of the surgical tool in order to rotate the surgical blade.

16. A surgical tool comprising:
a housing comprising a driver;
a surgical blade configured to be bi-directionally rotated by the driver; and
a footplate configured to receive the surgical blade, the footplate comprising:
a bottom portion configured to rest on ocular tissue of a patient's eye, wherein the bottom portion comprises a first slot configured to allow passage of a portion of the surgical blade through the bottom portion of the footplate and into the ocular tissue of the patient's eye, wherein the bottom portion further comprises a second slot configured to allow passage of at least a tip of the surgical blade through the bottom portion of the footplate;
multiple walls comprising multiple openings, the openings configured to receive additional portions of the surgical blade such that the surgical blade is rotatable relative to the footplate; and
an additional opening or open side configured to allow viewing of the surgical blade and at least one of the slots during use.

17. The surgical tool of claim 16, wherein:
the multiple walls comprise first and second walls located along opposite sides of the footplate;
the first wall includes a first opening configured to receive a projection from the surgical blade; and
the second wall includes a second opening configured to receive a central portion of the surgical blade that includes or is coupled to a gear.

18. A method comprising:
coupling a surgical blade to a footplate; and
coupling the footplate to a surgical tool;
wherein the footplate comprises:
a bottom portion configured to rest on ocular tissue of a patient's eye, the bottom portion comprising a slot configured to allow passage of a portion of the surgical blade through the bottom portion of the footplate and into the ocular tissue of the patient's eye;
first and second walls located along opposite sides of the footplate, the first wall comprising a first opening, the second wall comprising a second opening, the first opening configured to receive a projection from the surgical blade and the second opening configured to receive a central portion of the surgical blade that includes or is coupled to a gear such that the surgical blade is rotatable relative to the footplate; and
an additional opening or open side configured to allow viewing of the surgical blade and the slot during use.

19. The method of claim 18, further comprising:
coupling the gear to the central portion of the surgical blade.

20. The method of claim 18, wherein coupling the footplate to the surgical tool comprises:
inserting the gear into a shaft of the surgical tool so that the gear is able to engage a drive belt within the shaft of the surgical tool; and
coupling a flange extending from the second wall to the shaft.

* * * * *